US012649816B2

(12) United States Patent
Urraca et al.

(10) Patent No.: US 12,649,816 B2
(45) Date of Patent: Jun. 9, 2026

(54) THERMOPLASTIC POLYURETHANES DERIVED FROM LIGNIN MONOMERS

(71) Applicant: VITO NV, Mol (BE)

(72) Inventors: Ortiz Pablo Urraca, Mol (BE); Richard Vendamme, Mol (BE)

(73) Assignee: VITO NV, Mol (BE)

( * ) Notice: Subject to any disclaimer, the term of this patent is extended or adjusted under 35 U.S.C. 154(b) by 780 days.

(21) Appl. No.: 17/995,521

(22) PCT Filed: Apr. 6, 2021

(86) PCT No.: PCT/EP2021/058943
§ 371 (c)(1),
(2) Date: Oct. 5, 2022

(87) PCT Pub. No.: WO2021/204803
PCT Pub. Date: Oct. 14, 2021

(65) Prior Publication Data

US 2024/0270897 A1 Aug. 15, 2024

(30) Foreign Application Priority Data

Apr. 7, 2020 (EP) .................................... 20168400

(51) Int. Cl.
*C07C 43/23* (2006.01)
*C08G 18/64* (2006.01)

(52) U.S. Cl.
CPC .......... *C08G 18/6492* (2013.01); *C07C 43/23* (2013.01)

(58) Field of Classification Search
CPC .. C08G 18/6492; C08G 18/724; C08G 18/73; C08G 18/7664; C07C 43/23
See application file for complete search history.

(56) References Cited

U.S. PATENT DOCUMENTS

| | | | | |
|---|---|---|---|---|
| 5,491,210 | A | 2/1996 | Onwumere et al. | |
| 2021/0269616 | A1* | 9/2021 | Sels | C07G 1/00 |
| 2023/0235111 | A1* | 7/2023 | Urraca | C08G 18/73 528/1 |

FOREIGN PATENT DOCUMENTS

| | | | |
|---|---|---|---|
| CN | 102504179 | A | 6/2012 |
| JP | S60114797 | A | 6/1985 |
| JP | S60118327 | U | 8/1985 |

(Continued)

OTHER PUBLICATIONS

International Search Report and Written Opinion mailed Oct. 15, 2021 in reference to co-pending Application No. PCT/EP2021/058943 filed Apr. 6, 2021.

(Continued)

*Primary Examiner* — Jiangtian Xu

(74) *Attorney, Agent, or Firm* — DINSMORE & SHOHL LLP

(57) ABSTRACT

In general the present invention relates to thermoplastic polyurethanes containing lignin-derived monomers, lignin model compounds or the products of their respective functionalization in their structure. More specifically, this process relates to the use of 4-hydroxylalkylphenols and their derivatives as lignin-derived monomers or lignin model compounds. These can act either as chain extenders or be part of the polyol. The thermoplastic polyurethanes can be partially or fully bio-based. Furthermore, the invention relates to a method for preparing these thermoplastic polyurethanes and to their use.

15 Claims, 2 Drawing Sheets

(56) References Cited

FOREIGN PATENT DOCUMENTS

| | | | | | |
|---|---|---|---|---|---|
| JP | 2009019081 | A | * | 1/2009 | ............ C08G 18/40 |
| JP | WO2010087427 | A1 | | 8/2012 | |
| JP | 2020154675 | A | | 4/2019 | |
| WO | 2015205020 | A1 | | 11/2018 | |
| WO | 2020002361 | A1 | | 1/2020 | |

OTHER PUBLICATIONS

Chen, et al., "Preparation of lignin/glycerol-based bis(cyclic carbonate) for the synthesis of polyurethanes", Green Chemistry, vol. 17, pp. 4546-1551 2015.
Jeong, et al., "Preparation and Characterization of Thermoplastic Polyurethanes Using Partially Acetylated Kraft Lignin", Fibers and Polymers, vol. 14, No. 7, pp. 1082-1093, 2013.
Wallis, et al., "Hydroxyethylation of lignin in mechanical pulps", Appita, vol. 36, No. 3, pp. 192-196, 1981.
Zhang, et al., "Recent Advances on Lignin-Derived Polyurethane Polymers", Rev. Adv. Mater Sci., vol. 40, pp. 146-154, 2015.
Feghali, et al., "Thermosetting Polymers from lignin Model Compounds and Depolymerized Lignins", Topics in Current Chemistry, vol. 376, No. 32, pp. 1-25, 2018.
Oulame, et al., "Renewable alternating aliphatic-aromatic poly(ester-urethane)s prepared from ferulic acid and bio-based diols", European Polymer Journal, pp. 1-13, 2015.
Sun, et al., "Bright Side of Lignin Depolymerization: Toward New Platform Chemicals", Chemical Reviews, vol. 118, pp. 614-678, 2018.
Schutyser, et al., "Chemicals from lignin: an interplay of lignocellulose fractionation, depolymersation, and upgrading", Chemical Soc. Rev., vol. 47, pp. 852-908, 2018.
Linares, et al., "Solid-Support-Bound 1-Aminomidazolium Chlorochromate: A Selective, Efficient and Recyclable Oxidant", Synthesis, Vo. 3, pp. 382-388, 2001.
Pepper, et al., "Lignin and Related Compounds. III. An Improved Synthesis of 3-(4-Hydroxy-3-methoxyphenyl)-1-propanol and 3-(4-Hydroxy-3, 5-dimethoxyphenyl)-1propanol", Canadian Journal of Chemistry, vol. 49, p. 3394, 1971.
Zhao, et al., "Sustainable Aromatic Aliphatic Polyesters and Polyurethanes Prepared from Vanillin-Derived Diols via Green Catalysis", Polymers, vol. 12, pp. 1-16, 2020.

* cited by examiner

THERMOPLASTIC POLYURETHANES DERIVED FROM LIGNIN MONOMERS

CROSS REFERENCES TO RELATED APPLICATIONS

This application is a national-stage application under 35 U.S.C. § 371 of International Application No. PCT/EP2021/058943, filed Apr. 6, 2021, which International Application claims benefit of priority to European Patent Application No. 20168400.8, filed Apr. 7, 2020.

TECHNICAL FIELD

In general the present invention relates to thermoplastic polyurethanes containing lignin-derived monomers, lignin model compounds or the products of their respective functionalization in their structure. More specifically, this process relates to the use of 4-hydroxylalkylphenols and their derivatives as lignin-derived monomers or lignin model compounds. These can either act as chain extenders or be part of the polyol. The thermoplastic polyurethanes can be partially or fully bio-based. Furthermore, the invention relates to a method for preparing these thermoplastic polyurethanes and to their use.

BACKGROUND

Polyurethanes are widely used polymers for applications such as coatings, molded articles, foams (rigid and flexible), sealants and synthetic fibers, among others. Current synthetic polyurethanes are the result of the reaction between di or polymeric isocyanate monomers and monomers containing hydroxyl group (diols, triols or polyols).

Lignin is the second largest biopolymer on earth, second only to cellulose. However, contrary to the later, lignin is not currently valorized. Due to its high content of hydroxyl groups (both aliphatic and aromatic), it has been pursued as polyol replacement in polyurethane synthesis (Rev. Adv. Mat. Sci. 2015, 40, 146-154). However, lignins derived from cellulose isolation, also known as technical lignins, have a high molecular weight and polydispersity due to the condensation that takes place in the harsh reaction conditions of cellulose isolation. As a result, these type of lignins typically lead to poor performance polymers. Depolymerization or fractionation of lignin allows to obtain low molecular weight oligomers, with increase hydroxyl functionality, which results in polyurethane polymers with improved properties. Several scientific articles have proven this concept (*Top Curr Chem,* 2018, 373: 32) and there are patents as well (WO2018205020A1). Depolymerized lignin might be chemically modified prior to polyurethane synthesis as well, as shown in patents US20160145285A1 and US20170121458A1.

Despite the advantages of depolymerized lignin over non-depolymerized lignin, still most depolymerization protocols use high temperatures and acidic/basic media, which results in low yields of monomers. In fact, the use of lignin-derived monomers for polyurethane synthesis is the ideal scenario, as it allows defined structure and the possibility for drop-in replacement of petrol-derived monomers. Some lignin model compounds have been used in polyurethane synthesis, such as dimerized ferulic acid (*Eur. Polym. J.* 2015, 63, 186-193) or dimerized cresol (*Green Chem.* 2015, 17, 4546-4551)

Recently, new technologies that allow the isolation of monomers from lignin in good yields and selectivity have been developed, based on mild fractionation and/or depolymerization conditions and strategies to stabilize the intermediates formed during depolymerization (*Chem. Rev.* 2018 118, 614*; Chem. Soc. Rev.* 2018, 47, 852). These monomers can be divided into two big categories depending on the terminal group on the alkyl chain: 4-alkylphenols and 4-hydroxylalkylphenols. This patent is directed to the use of 4-hydroxyalkylphenols (Formula Ia) and their derivatives (Formula Ib) for polyurethane synthesis.

Formula Ia

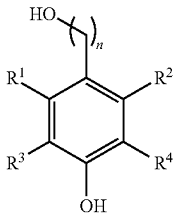

$R^1$ and $R^2$ independently represent H or $CH_3$ $R^3$ and $R^4$ independently represent H or $OCH_3$ n=0-3

The use of these monomers brings a new possibility for polyurethane synthesis, as it allows the bio-based molecule to serve as diol replacement. The lignin derived diol can be used as chain extender and/or as part of the polyol. By using lignin-derived monomers as diols, (partially) bio-based thermoplastic polyurethanes (hereafter TPU) can be produced. Contrary to standard polyurethanes, TPU typically consist of linear segmented block copolymers composed of alternating hard and soft segments. The hard segments are the result of the reaction between diisocyanates with short-chain diols, so-called chain-extenders in the field, while the soft segment is constituted by the long-chain diols, so-called polyols in the field. In this patent, both lignin-derived 4-hydroxyalkylphenol molecules and petroleum-derived 4-hydroxyalkylphenol model compounds of formula I, both termed 4-hydroxyalkylphenol derived monomers from lignin and represented by formula I, are used as short-chain diols, i.e. as chain-extenders to form TPU, or as part of the soft phase. TPU need to have a linear chain and therefore, monomers with two hydroxyl groups, i.e. diols, are required. Consequently, the use of lignin in its macromolecular form or the oligomers derived from its depolymerization, are not suitable. Although thermoplastic behavior has been reported in TPU formed from partially acetylated lignin (*Fibers and Polymers,* 2013, 14, 1082-1093), the macromolecular lignin does not allow a precise control over the hydroxyl value, and consequently over the properties of the polymer formed.

TPU typically display high elasticity combined with high mechanical strength, high impact properties, high abrasion resistance, low-temperature performance and oil and grease resistance. These properties make them suitable for a wide range of applications such as sporting goods, medical devices, mobile electronic devices, keyboard protectors for laptops, automotive instrument panels, caster wheels, power tools, footwear, performance films, wire and cable jacketing, adhesive and textile coating applications and 3D printing. The novel, fully or partially bio-based TPU can be used for the above listing applications.

There is no prior art on the use of structures in Formula I for polyurethane synthesis, neither the functionalization of those structures for a subsequent polyurethane synthesis. There are examples of functionalization of similar structures (4-hydroxylalkyl-phenols), but not with the goal of making them polymerizable monomers. There are some reports of the functionalization of the phenolic hydroxyl to anchor an aliphatic hydroxyl to it, so a bi-aliphatic diol is formed. In the patent WO2015126862A1 there is one example of synthesizing 4-(3-Hydroxypropoxy)benzeneethanol by reacting 2-(4-Hydroxyphenyl)ethanol with ethylene carbonate or with 3-chloro-1-propanol. In the scientific article *Synthesis* 2001, 382-388, 4-hydroxybenzenemethanol is reacted with 3-Bromo-1-propanol to yield 4-(3-Hydroxypropoxy)benzenemethanol. In the scientific article *Appita* 1982, 3, 192-196, 4-(3-Hydroxypropyl)-2-methoxyphenol was reacted with ethylene oxide to give 3-(4-(2-hydroxyethoxy)-3-methoxyphenyl)propan-1-ol.

It is accordingly an object of the present invention to provide the use of 4-hydroxyalkylphenol derived monomers from lignin as diols in the synthesis of thermoplastic polyurethanes (TPU), wherein said 4-hydroxyalkylphenol derived monomers from lignin can be represented by formula I Formula I

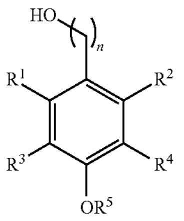

$R^1$ and $R^2$ independently represent H or alkyl; in particular H or $C_{1-6}$alkyl; more in particular H or CH3

$R^3$ and $R^4$ independently represent H or oxy-alkyl; in particular H or oxy-$C_{1-6}$alkyl; more in particular H or $OCH_3$ $R^5$ represents H or hydroxyalkyl; in particular H or hydroxy-$C_{1-12}$alkyl n=0-3

SUMMARY

Depolymerization of lignin can lead to 4-hydroxyalkylphenol monomers described in Formula Ia. These compounds can also be synthesized from petroleum-based chemicals. 4-hydroxyalkylphenol monomers can be functionalized to have two aliphatic diols, rendering the functionalized 4-hydroxyalkylphenol monomers (Formula Ib). Either 4-hydroxyalkylphenols (Formula Ia above) or the product of their derivatization (Formula Ib) can be used as short-chain diols (also termed chain extenders) or as part of the polyol mixture in the synthesis of TPU.

Formula Ib

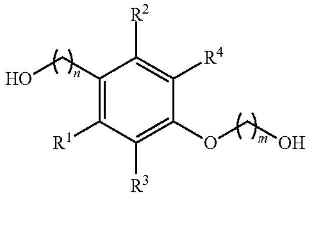

Wherein;

$R^1$ and $R^2$ independently represent H or alkyl; in particular H or $C_{1-6}$alkyl; more in particular H or $CH_3$;

$R^3$ and $R^4$ independently represent H or oxy-alkyl; in particular H or oxy-$C_{1-6}$alkyl; more in particular H or $OCH_3$;

n=0-3;

m=1-12

The lignin derived monomers or the products of their functionalization, commonly defined as in Formula I, are one of the components of the reaction mixture which also includes a diisocianate and long-chain diol (also termed polyol). If the lignin derived monomers are used as chain extenders, the composition can also include an additional chain extender. Optionally, one or more catalyst are added. By varying the type and ratio of the different reagents fine tuning of the chemical and physical properties of the TPU can be obtained. The method for to synthesize the TPU may be conducted utilizing conventional processing equipment, catalysts, and processes. In this process the different components might be bio-based.

The polymerization techniques useful for making the TPUs of this invention include conventional methods, such as reaction extrusion, batch processing, solution polymerization, reaction injection molding and cast polymerization. The (partially) bio-based TPU can serve as a replacement of petroleum-based TPU.

In a first aspect the present invention provides the use of lignin-derived monomers, lignin model compounds or the products of their respective functionalization according to formula I, in the synthesis of a thermoplastic polyurethane (TPU); wherein Formula I

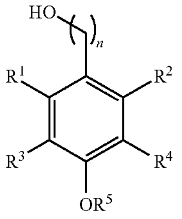

$R^1$ and $R^2$ independently represent H or alkyl; in particular H or $C_{1-6}$alkyl; more in particular H or CH3

$R^3$ and $R^4$ independently represent H or oxy-alkyl; in particular H or oxy-$C_{1-6}$alkyl; more in particular H or $OCH_3$ $R^5$ represents H or hydroxyalkyl; in particular H or hydroxy-$C_{1-12}$alkyl n=0-3

In another aspect the present invention provides the thermoplastic polyurethane (TPU) obtained thereof, i.e. comprising lignin-derived monomers, lignin model compounds or the products of their respective functionalization according to formula I.

The synthesis of the thermoplastic polyurethane (TPU) according to invention at least comprises the reaction product of a (a) an isocyanate composition; (b) lignin-derived monomers, lignin model compounds or the products of their respective functionalization according to any one of formula I, Ia, or Ib and (c) a polyol composition. In this reaction the lignin-derived monomers, lignin model compounds or the products of their respective functionalization according to any one of formula I, Ia, or Ib, function as chain extender. In one embodiment no further chain extenders are being used. In another embodiment additional chain extenders are being used.

In the lignin depolymerization process, polyols comprising the lignin-derived monomers, lignin model compounds or the products of their respective functionalization according to any one of formula I, Ia, or Ib, could equally be obtained. In the synthesis of the thermoplastic polyurethane (TPU) according to invention, such polyols could be used as one of the reagents, hence in one embodiment the TPU according to the invention is the reaction product of (a) an isocyanate; (b) a polyol composition containing lignin-derived monomers, lignin model compounds or the products of their respective functionalization according to any one of formula I, Ia, or Ib as repeating unit; (c) a chain extender. Such polyols can be used in isolation or combined with other polyols. Thus, in a further embodiment the TPU is the reaction product of (a) an isocyanate; (b) a polyol mixture, in which at least one of the polyols contains lignin-derived monomers, lignin model compounds or the products of their respective functionalization according to any one of formula I, Ia, or Ib as repeating unit; (c) a chain extender.

As for the polyol also the chain extender could either be the lignin-derived monomers, lignin model compounds or the products of their respective functionalization according to any one of formula I, Ia, or Ib, or a combination with further chain extenders. In one embodiment the thermoplastic polyurethane (TPU) according to the invention comprises the reaction product of (a) an isocyanate; (b) a polyol mixture, in which at least one of the polyols contains lignin-derived monomers, lignin model compounds or the products of their respective functionalization according to any one of formula I, Ia, or Ib as repeating unit; (c) lignin-derived monomers, lignin model compounds or the products of their respective functionalization according to any one of formula I, Ia, or Ib acting as a chain extender; optionally in combination with an additional chain extender.

In the synthesis of the thermoplastic polyurethane (TPU) according to the invention the isocyanate composition preferably comprises an aromatic diisocyanate, an aliphatic diisocyanate, a cycloaliphatic diisocyanate or mixture of any of them.

In a particular embodiment according to the invention the lignin-derived monomers, lignin model compounds or the product of their respective functionalization used in the synthesis of the TPU's according to the invention comprise the following structures Formula Ia

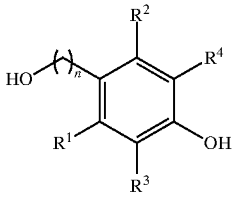

Lignin-derived monomer

Formula Ib

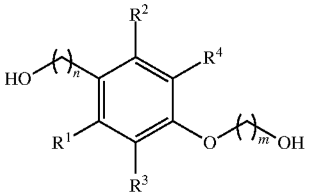

Functionalized lignin-derived monomer

Wherein;

$R^1$ and $R^2$ independently represent H or alkyl; in particular H or $C_{1-6}$alkyl; more in particular H or $CH_3$;

$R^3$ and $R^4$ independently represent H or oxy-alkyl; in particular H or oxy-$C_{1-6}$alkyl; more in particular H or $OCH_3$;

$$n = 0\text{–}3;$$

$$m = 1\text{–}12$$

In a particular embodiment the lignin-derived monomers or the products of their functionalization as defined in the different embodiments herein before, are present as an extract of depolymerized lignin comprising at least 80% weight of lignin-derived monomers of formula I, Ia, or Ib; more in particular as an extract of depolymerized lignin comprising at least 80% weight; even more particular at least 90% weight of lignin-derived monomers of formula III.

In a particular embodiment the polyol composition as used in the synthesis of the TPU's according to the invention comprises a polyether polyol, polyester polyol, polyacrylated polyol, polycarbonate polyol, polysiloxane polyol or mixtures thereof, with a molecular weight from 200 to 8000.

As mentioned above, the polyol composition could be based or comprise lignin-derived monomers, lignin model compounds or the products of their respective functionalization according to formula I, Ia, or Ib as a repeating unit. Thus in one embodiment the polyol composition comprises lignin-derived monomers, lignin model compounds or the products of their respective functionalization according to any one of formula I, Ia, or Ib as a repeating unit, optionally further comprising polyether polyol, polyester polyol, polyacrylated polyol, polycarbonate polyol, polysiloxane polyol or mixtures thereof, with a molecular weight from 200 to 8000.

The lignin-derived monomers or the products of their functionalization as defined in the different embodiments herein, act as chain extenders in the synthesis of the TPU's according to the invention, optionally in combination with additional chain extenders. In a particular embodiment the additional chain extender composition comprises diols, diamines, and combinations thereof with 2 to 12 carbon atoms.

Relying on lignin based materials, one, several or all components within the TPU's according to the invention could be or are bio-based. The equivalents of diisocyante to active hydrogen containing components are typically in ranges from 0.3 to 2. The molar ratio of the polyol component to the total chain extenders (lignin-derived monomers+additional chain extenders) typically ranges from 99:1 to 1:99. In one embodiment the molar ratio of (functionalized) lignin-derived monomer to the additional chain extender ranges from 99:1 to 1:99.

The TPU's as described herein could be obtained by reaction extrusion, batch processing, solution polymerization, reaction injection molding and cast polymerization; and can be used in different applications, mainly as a replacement of petroleum-based thermoplastic polyurethanes.

In a further embodiment the present invention provides an extract of depolymerized lignin oil comprising at least 80% weight; in particular at least 90% weight of monomers according to formula III; as well as the use of said extracts or of the monomer(s) as defined herein, i.e. the monomers of formula I, Ia, or Ib, in the synthesis of thermoplastic polyurethanes.

DETAILED DESCRIPTION

Figure 1:
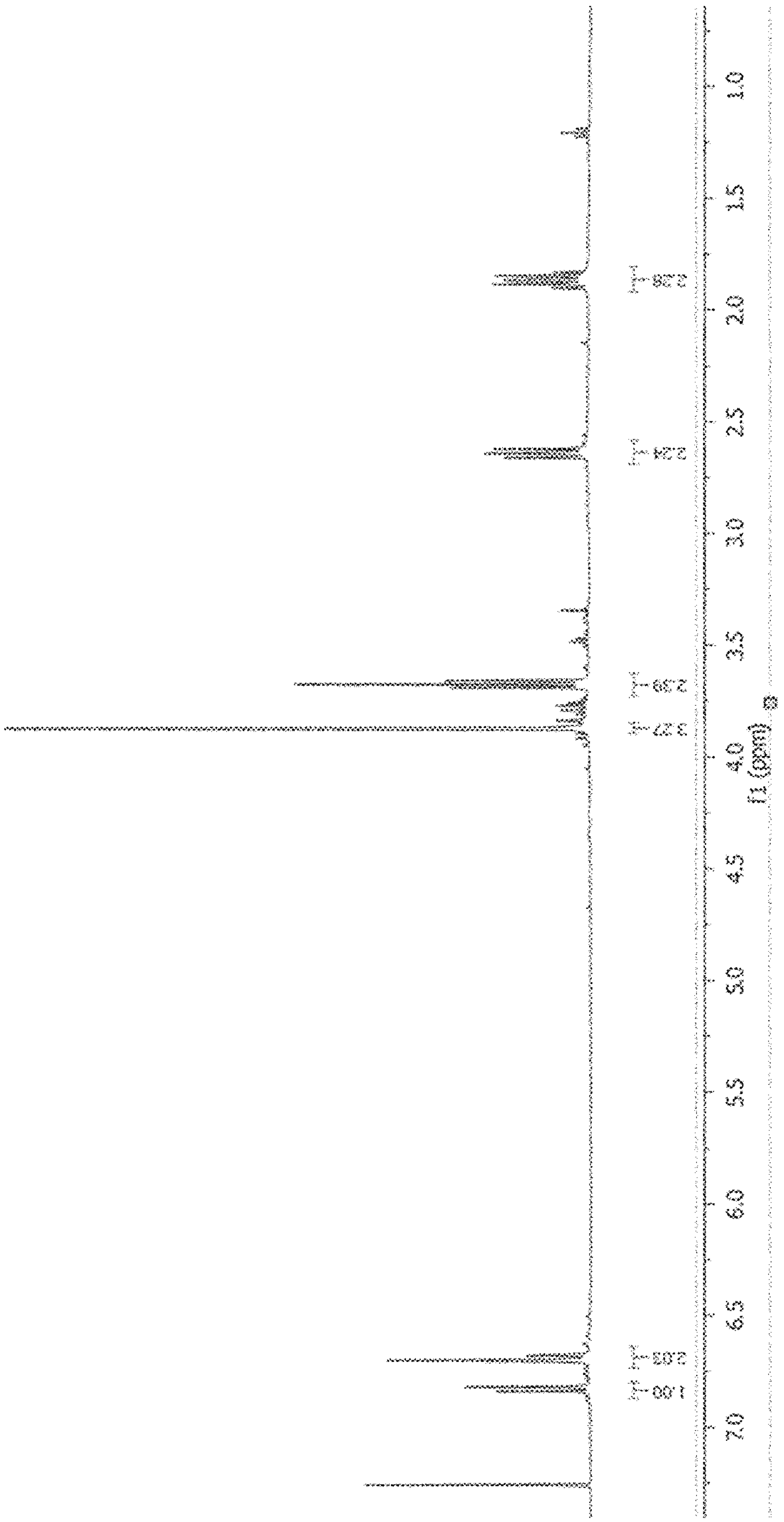
FIG. 1 is a $^1$H NMR spectrum of highly enriched mixture in DCA extracted from lignin.

The TPU of the present invention includes in their composition lignin-derived monomers, lignin model compounds or the products of their respective functionalization. As already mentioned herein before, in this invention, lignin-derived monomers, lignin model compounds or the products of their respective functionalization, generally represented by formula I and referred to as 4-hydroxyalkylphenol derived monomers from lignin, are used as short-chain diols (also termed chain extenders) or as part of the polyol mix, in the synthesis of TPU.

In a first embodiment, the TPU of the present invention includes the reaction product of (a) an isocyanate; (b) 4-hydroxyalkylphenol derived monomers from lignin as defined in any one of formula I, Ia, or Ib; and (c) an optional long chain diol (polymeric diol, also termed polyol in the field).

Besides the lignin derived monomers also other chain extenders could be used in the synthesis of the TPU's. Thus in a second embodiment, the TPU of the present invention includes the reaction product of (a) an isocyanate; (b) 4-hydroxyalkylphenol derived monomers from lignin as defined in any one of formula I, Ia, or Ib; (c) a long chain diol (polymeric diol, also termed polyol in the field); and (d) an additional chain extender.

In a third embodiment, the TPU of the present invention includes the reaction product of (a) an isocyanate; (b) a long chain diol (polymeric diol, also termed polyol in the field) containing 4-hydroxyalkylphenol derived monomers from lignin as defined in any one of formula I, Ia, or Ib as repeating unit; and (c) a chain extender.

In a fourth embodiment, the TPU of the present invention includes the reaction product of (a) an isocyanate; (b) a mixture of long chain diols (polymeric diols, also termed polyols in the field) out of which at least one contains 4-hydroxyalkylphenol derived monomers from lignin as defined in formula I as repeating unit; and (c) a chain extender.

In a fifth embodiment, the TPU of the present invention includes the reaction product of (a) an isocyanate; (b) a mixture of long chain diols (polymeric diols, also termed polyols in the field) out of which at least one contains 4-hydroxyalkylphenol derived monomers from lignin as defined in formula I as repeating unit; and (c) 4-hydroxyalkylphenol derived monomers from lignin as defined in any one of formula I, Ia, or Ib acting as chain extenders.

In each of the foregoing embodiments the 4-hydroxyalkylphenol derived monomers from lignin can be 4-hydroxyalkylphenols (Formula Ia); their derivatives (Formula Ib) or even combinations thereof. In a particular embodiment the 4-hydroxyalkylphenol derived monomers from lignin used in the synthesis of the TPU's can be either a 4-hydroxyalkylphenols according to Formula Ia; or a derivative according to Formula Ib.

In each of the foregoing embodiments, by varying the type and ratio of the different reagents fine-tuning of the chemical and physical properties of the TPU can be obtained. The method to synthesize the TPU may be conducted utilizing conventional processing equipment, catalysts, and processes. In this process the different components might be bio-based.

Diisocyanate Composition

In one embodiment, the isocyanate suitable for synthesizing the TPU is any of the isocyanates previously disclosed as suitable in the preparation of TPU, and include aliphatic, aromatic and cycloaliphatic diisocyanates, and mixtures thereof.

Illustrative diisocyanates include, but are not limited to methylenebis(phenyl isocyanate) including the 4,4'-isomer, the 2,4'-isomer and mixtures thereof; 2,4- and 2,6-toluene diisocyanate and mixtures thereof; m- and p-phenylene diisocyanates; chlorophenylene diisocyanates; a,a'-xylylene diisocyanate; o-tolidine diisocyanate; 1,5-naphthalene diisocyanate; hexamethylene 1,6-diisocyanate; pentamethylene 1,5-diisocyanate; 1,4-butane diisocyanate; isophorone diisocyanate; methylenebis(cyclohexyl isocyanate) including the 4,4'-isomer, the 2,4'-isomer and mixtures thereof; cyclohexylene diisocyanates (1,2-; 1,3-; or 1,4- and mixtures thereof). Also included are the modified forms of methylenebis(phenyl isocyanate) that enable them to be stable liquids at ambient temperature. Dimers and trimers of the above diisocyanates may also be used in the TPU synthesis.

More preferably, the diisocyanates are selected from methylenebis(phenyl isocyanate) including the 4,4'-isomer, the 2,4'-isomer, and mixtures thereof; 2,4- and 2,6-toluene diisocyanate and mixtures thereof; hexamethylene 1,6-diisocyanate; pentamethylene 1,5-diisocyanate; methylenebis (cyclohexyl isocyanate) including the 4,4'-isomer, the 2,4'-isomer and mixtures thereof.

The Lignin-Derived Monomers

In one embodiment, the lignin-derived monomers in Formula Ia and/or the products of their functionalization (Formula Ib), are used as chain extender in the synthesis of TPU. In a particular embodiment the lignin-derived monomers are those as defined in formula III and the functionalized lignin-derived monomers are those as defined in formula IV Lignin-Derived Monomer Functionalized Lignin-Derived Monomer Formula III

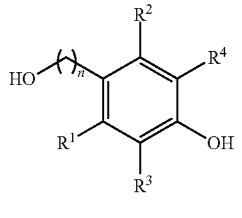

Lignin-derived monomer

Formula IV

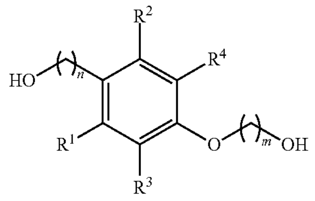

Functionalized lignin-derived monomer

Wherein;

$R^1$ and $R^2$ independently represent H or $CH_3$; $R^3$ and $R^4$ independently represent H $OCH_3$;

n=0-3; and m=1-12

In one embodiment, the lignin-derived monomers as defined in any one of formulas I, Ia, or Ib are used as such in TPU synthesis. The composition of monomers in the depolymerized lignin will depend on the type of lignocellulose that is chosen as starting material and on the depolymerization conditions and reactions. Some types of depolymerization methods, especially reductive catalytic methods, allow the isolation of 4-hydroxylalkylphenols as defined in formulas I, Ia or Ib in good yields.

Typically, however, the 4-hydroxylalkylphenols as defined in formulas I, Ia or III are obtained as mixture of monomers (variation in positions $R^1$, $R^2$, $R^3$ and $R^4$) wherein $R^1$ and $R^2$ are each independently H or $CH_3$ and $R^3$ and $R^4$ are each independently H or $OCH_3$. The most prevalent 4-hydroxylalkylphenols monomers are those according to Formula Ia wherein $R^1$ and $R^2$=H; $R^3$=$OCH_3$; $R^4$=H or $OCH_3$; n=3. Such mixtures of monomers can be used in the described protocol.

However, depolymerization of lignin does not uniquely deliver these type of monomers, namely 4-hydroxylalkylphenols, but also other monomers such as 4-alkylphenols (R=$CH_3$) and higher molecular weight molecules (dimers, oligomers). 4-hydroxylalkylphenols can be separated from 4-alkylphenols by chemical or physical means, but it is possible that some 4-alkylphenols remain in the monomer mixture. On the other hand, if there are trifunctional monomers or oligomers in the mixture, they can act as branching elements, leading to a branched or partially cross-linked polymer. When using the mixture of monomers enriched in 4-hydroxylalkylphenols as chain extender, a thermoplastics material can be obtained by lowering the polyol to diisocyanate ratio under 1. Besides lignin-derived monomers, lignin model compounds can be used. Lignin model compounds are petroleum-derived compounds whose structure reproduce the lignin-derived molecules. Thus, although their origin is different their molecular structure, and therefore the properties of the resulting polymer, are the same. Consequently, in this patent, they are included under lignin-derived monomers term.

In one embodiment, the lignon-derived monomers are functionalized to obtain a di-aliphatic diol (Formulas Ib). This reaction can be performed with different chemicals, such as but not limited to cyclic ethers such as ethylene oxide, propylene oxide, butylene oxide, tetrahydrofuran or 5-methyl-tetrahydrofuran; cyclic carbonates such as ethylene carbonate and propylene carbonate; haloalcohols such as 2-chloroethanol, 2-iodoethanol, 3-chloro-1-propanol, 3-bromo-1-propanol and 4-chlorobutanol, 5-bromo-1-pentanol, 6-chlorohexanol, 8-chloro-1-octanol, 10-chloro-1-decanol.

The selective functionalization of phenolic hydroxyl group can be achieved in different ways. One option is by using a base that will deprotonate the phenolic hydroxyl but not the aliphatic hydroxyl. Examples of common bases that meet this criteria include, but are not limited to: ammonia, metal hydroxides $M(OH)_x$, preferentially alkali metal hydroxides (such NaOH or KOH); carbonate salts with the formula $M_x(CO_3)_y$ (such as $Na_2CO_3$ or $K_2CO_3$).

In one embodiment, the lignin-derived monomers and functionalized lignin-derived monomers might be transformed to amino alcohols or diamines. Also these can be used in TPU synthesis.

The Short-Chain Diol (Chain Extender)

In some embodiments the lignin derived monomers act as the chain extenders. In other embodiments, a standard short-chain diol (chain extender) is used. In other embodiments, there are two chain extenders, one standard and one being the lignin-derived monomers. In this last case, the molar ratio of the 4-hydroxyalkylphenol derived monomers from lignin to the additional chain extender might between 99:1 to 1:99, preferably between 90:10 and 10:90, most preferably between 80:20 and 20:80. Additional chain extenders comprises diols, diamines, and combinations thereof with 2 to 12 carbon atoms.

Illustrative chain extenders include, but are not limited to ethylene glycol; diethylene glycol, propylene glycol; dipropylene glycol; 1,4-butanediol; 1,6-hexanediol; 1,3-butanediol; 1,5-pentanediol; neopentylglycol; 2-ethyl-2-butyl-1,3-propanediol; 1,4-cyclohexanedimethanol; hexamethylenediol; heptanediol; nonanediol; dodecanediol; benzenedimethanol (1,2-; 1,3-; or 1,4- and mixtures thereof); bis(2-hydroxyethoxy)benzene (1,2-; 1,3-; or 1,4- and mixtures thereof); ethylenediamine; butanediamine; 1,2-propylene diamine; 1,6-hexamethylenediamine; piperazine; ethanolamine; N-methyl-diethanolamine; N-ethyldiethanolamine; N-phenylpropanolamine and mixtures thereof.

The Long-Chain Diol (Polyol)

In some embodiments, the long-chain diol (also termed polyol) component suitable for synthesizing the TPU might be any from the categories of polyether polyols, polyester polyols, polyacrylated polyols, polycarbonate polyols or polysiloxane polyols or mixtures thereof with a molecular weight preferably from 200 to 8000, more preferably from 300 to 4000 and most preferably from 400 to 2000.

In one embodiment, the polyol may comprise a polyether polyol. Suitable polyether polyols may include polyether polyols derived from a diol or polyol reacted with an ether comprising an alkylene oxide, typically ethylene oxide or propylene oxide or mixtures thereof. Illustrative polyether polyols include, but are not limited to poly(ethylene glycol); poly(propylene glycol); poly(tetramethylene ether glycol), also known as poly-tetrahydrofuran. Suitable polyether polyols also include polyetheramines, especially diamines, and polyamide adducts such as the reaction product of ethylenediamine and propylene oxide. Copolyethers from the reaction of tetrahydrofuran and ethylene oxide or propylene oxide might also be used in the invention. The polyether composition might include a mixture of polyethers.

In one embodiment, the polyol might comprise a polyester polyol. Polyesters polyols are produced either by an esterification reaction of one or more glycols with one or more dicarboxylic acids or anhydrides; or by transesterification reaction of one or more glycols with esters of dicarboxylic acids. The dicarboxylic acids of the desired polyester can be aliphatic, cycloaliphatic, aromatic, or combinations thereof. Illustrative examples of dicarboxylic acids include, but are not limited to: succinic, glutaric, adipic, pimelic, suberic, azelaic, sebacic, dodecanedioic, isophthalic, terephthalic, cyclohexane dicarboxylic and mixtures thereof. Anhydrides of the above dicarboxylic acids such as phthalic anhydride, tetrahydrophthalic anhydride and mixtures thereof can also be used. The glycols which are reacted to form a desirable polyester intermediate can be aliphatic, aromatic, or combinations thereof, including any of the glycols described above in the chain extender section. Illustrative examples include ethylene glycol; 1,2-propanediol; 1,3-propanediol; 1,3-butanediol; 1,4-butanediol; 1,5- pentanediol; 1,6-hexanediol; neopentylglycol; 1,4-cyclohexanedimethanol; decamethylene glycol; dodecamethylene glycol, and mixtures thereof.

In one embodiment, the polyol might comprise a polyacrylated polyols.

In one embodiment, the polyol might comprise a polycarbonate polyol. Polycarbonate polyols can be produced by reacting diols, such as propylene glycol, 1,4-butanediol or 1,6-hexenediol or mixtures of them with diarylcarbonates.

In one embodiment, the polyol might comprise a polysiloxane polyols. Polysiloxane polyols can be produced by the dehydrogenation reaction between a polysiloxane hydride and an aliphatic polyhydric alcohol or a polyoxyalkylene alcohol. Illustrative examples include alpha-omega-hydroxypropyl terminated poly(dimethysiloxane); alpha-omega-amino propyl terminated poly(dimethysiloxane); copolymers of poly(dimethysiloxane) materials with a poly (alkylene oxide).

In one embodiment, the polyol from any of the above listed categories (polyether polyols, polyester polyols, polyacrylated polyols, polycarbonate polyols or polysiloxane polyols) comprises 4-hydroxyalkylphenol derived monomers from lignin as defined in formula I as at least one of the repeating units. The polyols containing lignin derived monomers might be synthesized according to any of the methods used for transforming diols into polyols In one embodiment, the polyol is a mixture of polyols of any of the above listed categories (polyether polyols, polyester polyols, polyacrylated polyols, polycarbonate polyols or polysiloxane polyols) where at least one of them comprises 4-hydroxyalkylphenol derived monomers from lignin as defined in formula I as at least one of the repeating units.

TPU Formulation

The overall equivalent ratio of the total diisocyanate to the total equivalent of the active hydrogen containing components (the lignin-derived monomers acting as short-chain diol, the optional further short-chain diol(chain extender) and the long-chain diol (polyol) ranges from 0.3 to 2, more preferably from 0.5 to 1.5 and most preferably 0.7 to 1.2. When lignin derived mixtures enriched in 4-hydroxyalkylphenols that contain molecules (dimers, oligomers) with functionality >2 are used, a ratio of diisocyante to isocyante reactive groups lower than 1 is used. Molar ratios of polyol to total short-chain diols (lignin-derived monomers plus optional chain extenders) might range preferably from 99:1 to 1:99, more preferably from 90:10 to 10:90, and most preferably from 80:20 to 20:80. The higher the ratio of short-chain diols, the harder the resulting TPU.

Catalysts that accelerate the reaction between the isocyanate groups and the isocyanate-reactive groups (hydroxyl or amine) are not compulsory, but might be used. Two types of catalysts can be independently used. Tertiary amines, such as but not limited to triethylamine; triethylenediamine; dimethylcyclohexylamine; N-methylmorpholine; N-ethylmorpholine; N,N,N',N'-tetramethylethylenediamine; N,N,N',N'-tetraethylethylenediamine; N,N-dimethylethanolamine; N,N-diethylethanolamine; N,N'-dimethylpiperazine; N,N,N',N'-tetramethylguanidine; N,N,N',N'-tetramethyl-1,3-butanediamine; 2-(dimethylaminoethoxy)ethanol diazabicyclo [2.2.2]octane and mixtures thereof. Organic metal compounds, such as but not limited to stannous octoate; stannous oleate; lead octoate; dibutyltin dioctoate; dibutyltin diluarate; dibutyltin diacetate; iron(III) acetylacetonate; magnesium acetyl acetonate; bismuth neodecanoate and mixtures thereof. The amount of catalyst used is generally within the range of 0.0001 to 1.0 percent by weight of the total weight of the reactants.

Besides catalysts, customary auxiliaries and additives can also be added into the components, into the reaction mixture or after making the TPU. Examples of those include, but are not limited to flame retardants, antioxidants, nucleating agents, stabilizers against hydrolysis, light, heat, oxidation or discoloration, surface-active substances, lubricants and mold release agents, dyes and pigments, inhibitors, antimicrobial agents, impact modifiers, rheology modifiers, UV absorbers, inorganic and/or organic fillers, reinforcing materials and plasticizers. Chain regulators can be used optionally added. These compounds have only one functional group reactive toward isocyanates.

The polymerization techniques useful for making the TPUs of this invention include conventional methods, such as reaction extrusion, batch processing, solution polymerization, reaction injection molding and cast polymerization.

The (partially) bio-based TPU can serve as a replacement of petroleum-based TPU, for example but not limited to sporting goods, medical devices, mobile electronic devices, keyboard protectors for laptops, automotive instrument panels, caster wheels, power tools, footwear, performance films, wire and cable jacketing, adhesive and textile coating applications and 3D printing

EXAMPLES

Lignin Derived Monomers

Lignin derived monomers may be extracted from lignin or synthesized from petroleum derived chemicals. The extraction of 4-(3-hydroxypropyl)-2-methoxyphenol (dihydroconiferyl alcohol, DCA) or 4-(3-hydroxypropyl)-2,6-dimethoxyphenol (dihydrosinapyl alcohol, DSA) might be performed according to the following method:

DCA and/or DSA can be extracted from depolymerized lignin oil containing this compound, following an extraction protocol.

In one embodiment, the DCA and/or DSA in the depolymerized lignin oil is extracted by water. The lignin oil is mixed with water in a mass ratio of preferably in 1:1 to 1:100 grams to ml ratio, more preferably 1:2 to 1:50, most preferably 1:5 to 1:20. The mixture of lignin in water can be heated up to the boiling point of water, and keep stirring for a certain time between 5 min and 72 h, preferably between 10 min and 48 h, most preferably between 20 min and 24 h. After the corresponding time, the mixture is let to cool and settle down and the water layer is collected, filtered. The remaining lignin might be again submitted to another extraction. Several extraction cycles can be performed to increase the yield of extracted monomer. The combined water layers are mixed and the water is removed, leading to a mixture highly enriched in DCA and/or DSA, together with some DCA and/or DSA dimers. Alternatively, extraction of DCA from the water phase using an organic solvent can be done, and then concentrate it. The mixture can be further purified by column chromatography or by crystallization.

Figure 2:
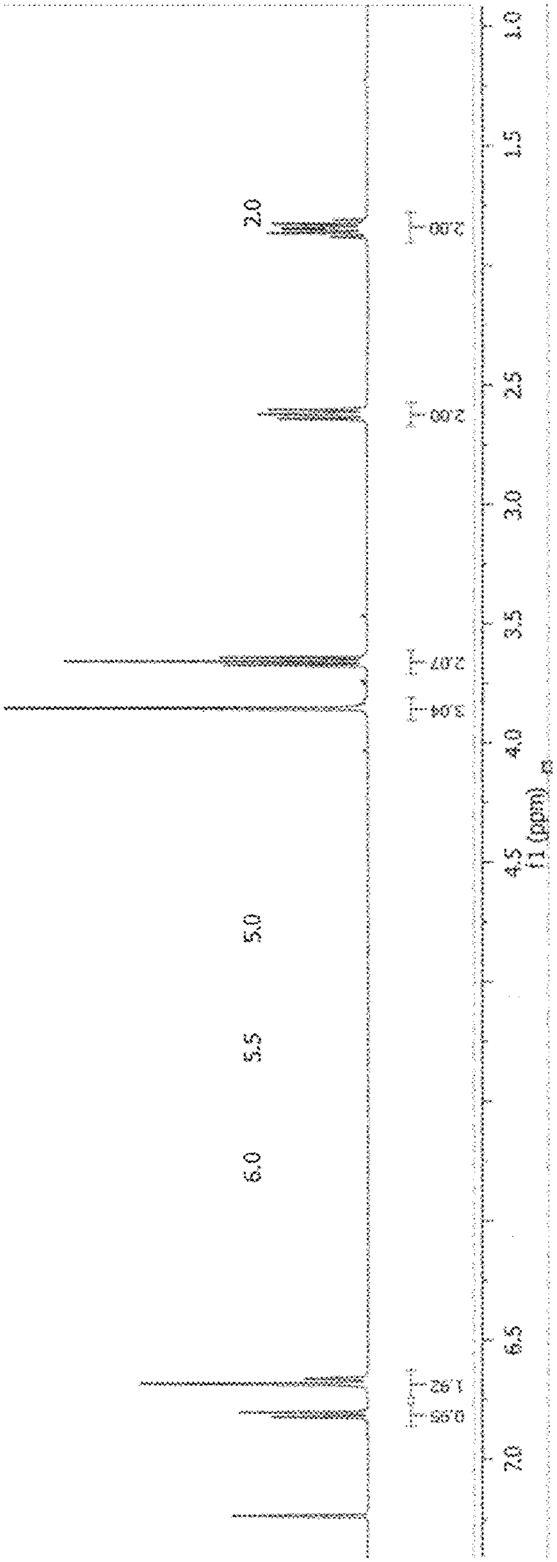
FIG. 2 is a $^1$H NMR spectrum of pure DCA extracted from lignin.

In another embodiment, depolymerized lignin oil might be first fractionated using an organic solvent in which DCA and/or DSA is soluble such as but no limited to diethyl ether, ethyl acetate, methanol, ethanol, tetrahydrofuran, dioxane, dichloromethane, acetone, ethyl methyl ketone. Apolar solvents such as hexanes and toluene are not suitable. Fractionation involves stirring an amount of lignin in a volume of solvent, preferably in 1:1 to 1:100 grams to ml ratio, more preferably 1:2 to 1:50, most preferably 1:5 to 1:20. The mixture of lignin in solvent might be heated up to the boiling point of the solvent. The stirring time is between 10 min and 72 h, preferably between 1 h and 48 h, most preferably between 2 h and 24 h. The soluble fraction is collected after filtration and the solvent removed. Sequential fractionations, using different solvents, are possible. The solvent fractionated lignin will be enriched in DCA and/or DSA compared to the starting lignin oil. This fraction is then fractionated with water. The lignin oil is mixed with water in a mass ratio of preferably in 1:1 to 1:100 grams to ml ratio, more preferably 1:2 to 1:50, most preferably 1:5 to 1:20. The mixture of lignin in water can be heated up to the boiling point of water, and keep stirring for a certain time between 5 min and 72 h, preferably between 10 min and 48 h, most preferably between 20 min and 24 h. After the corresponding time, the mixture is let to cool and settle down and the water layer is collected, filtered. The remaining lignin might be again submitted to another extraction. Several extraction cycles can be performed to increase the yield of extracted monomer. The combined water layers are mixed and the water is removed, leading to a mixture highly enriched in DCA and/or DSA, together with some DCA and/or DSA dimers (FIG. 1—1H NMR of highly enriched mixture in DCA extracted from lignin). Alternatively, extraction of DCA and/or DSA from the water phase using an organic solvent can be done, and then concentrate it. The mixture can be further purified by column chromatography, distillation or crystallization (FIG. 2-1H NMR of pure DCA extracted from lignin).

DCA and DSA can also be synthesized from petrol-derived chemicals (Example 1 and 2 respectively)

Example 1

4-(3-hydroxypropyl)-2-methoxyphenol, dihydroconiferyl alcohol (DCA)

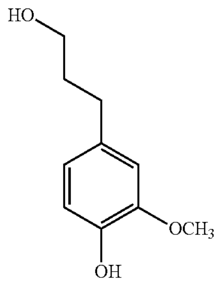 [SMILES: COc1cc(CCCO)ccc1O]

Following a modified literature procedure (*Can. J. Chem.* 1971, 49, 3394-3395) under anhydrous atmosphere eugenol (18.9 mL, 122.0 mmol) was dissolved in anhydrous THF. The mixture was cooled down to 0° C., followed by dropwise addition of borane dimethyl sulfide complex (15 mL, 158.2 mmol) over 20 minutes. After stirring for one hour at 0° C., the reaction mixture was carefully quenched using water (40 mL). Aqueous sodium hydroxide solution (3M, 48 mL) was added and the reaction mixture was again cooled down to 0° C. Aqueous hydrogen peroxide solution (30%, 28 mL) was added carefully and the solution was allowed to warm to room temperature, and it was left stirring for 1.5 hours. Afterwards, the mixture was poured into a beaker and diethyl ether was added causing the salt to precipitate. The two layers were decanted into a separation funnel and extractions using diethyl ether were performed. After two extractions the aqueous solution was acidified using hydrochloric acid, followed by two more extractions using diethyl ether. All organic layers were combined and washed using brine. The solvent was dried using magnesium sulfate, filtered and removed in vacuo. The obtained crude product was purified by recrystallization in chloroform/carbon disulfide mixture. Colorless crystals were obtained in 73% yield. $^1$H NMR (600 MHz, $CDCl_3$) δ 6.83 (d, J=7.9 Hz, 1H), 6.72-6.67 (m, 2H), 3.87 (s, 3H), 3.68 (t, J=6.4 Hz, 2H), 2.64 (t, J=7.6 Hz, 2H), 1.91-1.83 (m, 2H).

Example 2

4-(3-hydroxypropyl)-2,6-dimethoxyphenol, dihydrosinapyl alcohol (DSA)

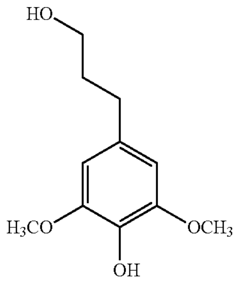 [SMILES: COc1cc(CCCO)cc(OC)c1O]

Under anhydrous atmosphere dihydrosinapic acid (8 gram, 35 mmol) was dissolved in anhydrous THF and cooled down to 0° C. Lithium aluminum hydride (3.00 gram, 79 mmol) was added portionwise over 1 hour. The reaction mixture was stirred at room temperature overnight. The reaction was quenched by slowly pouring it into ethyl acetate, followed by the addition of water. The aqueous layer was extracted with ethyl acetate, the organic layers were combined and washed using brine. The solvent was dried using magnesium sulphate, filtered and removed in vacuo. The product was obtained as yellow liquid in 91% yield. $^1$H NMR (400 MHz, $CDCl_3$) δ 6.42 (s, J=3.8 Hz, 2H), 3.86 (s, J=6.2 Hz, 6H), 3.67 (t, J=6.4 Hz, 2H), 2.63 (t, 2H), 1.91-1.82 (m, 2H).

Functionalization of Lignin-Derived Monomers

Whether synthetic or derived from lignin, 4-hydroxyalkylphenols can be functionalized Example 3

3-(4-(3-hydroxypropoxy)-3-methoxyphenyl)propan-1-ol, BA-DCA

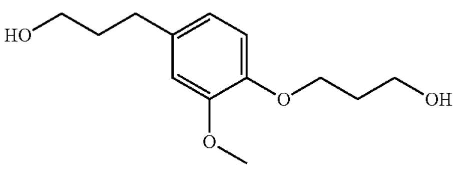 [SMILES: COc1cc(CCCO)ccc1OCCCO]

4-(3-hydroxypropyl)-2-methoxyphenol (4.00 gram, 22 mmol) was dissolved in isopropyl alcohol, followed by the addition of sodium hydroxide (1 gram, 26.5 mmol, 1.2 eq.). The mixture was stirred for 30 minutes, before 3-chloro-1-propanol (2.4 mL, 28 mmol, 1.3 eq.) was added. After addition of 3-chloro-1-propanol, the reaction flask was brought to reflux for at least 24 hours. When the reaction was done, the solvent was removed and water was added. The now aqueous mixture was extracted using ethyl acetate, and the organic phases were combined and washed using brine. The solvent was dried using magnesium sulphate, filtered and removed in vacuo. The crude was purified by column chromatography, using ethyl acetate as the mobile phase. The product was obtained as a clear liquid in 86% yield, and solidified afterwards as a white solid. $^1H$ NMR (600 MHz, $CDCl_3$) δ 6.82 (d, J=7.7 Hz, 1H), 6.73-6.70 (m, 2H), 4.16 (t, J=5.8 Hz, 2H), 3.87 (t, J=5.5 Hz, 2H), 3.83 (s, 3H), 3.67 (t, J=6.4 Hz, 2H), 2.75 (br), 2.65 (t, J=7.5 Hz, 2H), 2.05 (tt, J=5.8, 5.5 Hz, 2H), 1.87 (tt, J=7.5, 6.4 Hz, 2H), 1.71 (br). $^{13}C$ NMR (101 MHz, $CDCl_3$) δ 149.44, 146.40, 135.38, 120.37, 113.60, 112.08, 68.71, 62.29, 61.58, 55.90, 34.49, 31.89, 31.86.

Example 4

3-(4-(3-hydroxypropoxy)-3,5-dimethoxyphenyl)propan-1-ol, BA-DSA

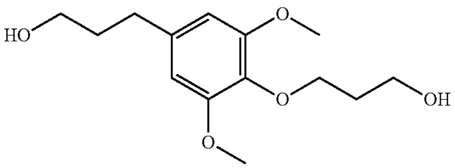 [SMILES: COc1cc(CCCO)cc(OC)c1OCCCO]

It was synthesized following the above described procedure for Example 3 using 4-(3-hydroxypropyl)-2,6-dimethoxyphenol as starting material. The product was obtained in 17% yield. $^1H$ NMR (400 MHz, $CDCl_3$) δ 6.42 (s, 2H), 4.11 (t, J=5.6 Hz, 2H), 3.91 (t, J=5.5 Hz, 2H), 3.83 (s, 6H), 3.69 (t, J=6.4 Hz, 2H), 3.37 (s, 1H), 2.66 (t, J=7.6 Hz, 2H), 2.06 (s, 1H), 1.99-1.84 (m, 4H). $^{13}C$ NMR (101 MHz, $CDCl_3$) δ 153.02, 138.00, 135.03, 105.36, 72.20, 62.17, 61.38, 56.09, 34.36, 32.64, 32.16.

Synthesis of the Polymers

Using the aforementioned lignin derived monomers (DCA and/or DSA) or the aforementioned functionalized lignin-derived monomers (BA-DCA and/or BA-DSA) TPUs can be synthesized according to the following general protocol: In a dried round bottom flask, the polyol (long-chain diol) was dissolved in dry DMF and stirred at from between and about 80° C. or 100° C. To this solution the diisocianate (MDI or HDI) was added and kept it reacting for 10-30 minutes. Afterwards the chain extender (lignin derived monomer, and if present the additional chain extender) were added followed by the catalyst (tin octanoate, 1 mol %). The mixture was kept reacting for 10 min-20 h; in particular for at least 3 h; more in particular for 3 h-20 h; and then precipitated in water and the solids, i.e. the polymer filtered off. The resulting polymer was then dried in a vacuum oven, or alternatively the filtered polymer was dissolved in THF, poured in a mold and dried in a vacuum oven.

Some of the polymers were characterized by gel permeation chromatography and differential scanning calorimetry. The polymers sometimes showed two glass transition temperatures, one of which, corresponding to the hard phase, was very weak. This is not listed in the table.

| Reaction | Monomer | Additional Chain extender | Polyol | Diisocyanate | MW | Tg |
|---|---|---|---|---|---|---|
| PO-295 | DCA (0.5) | | PolyTHF1000 (0.5) | MDI (1.05) | | −47 |
| PO-296 | DCA (0.5) | | PolyTHF1000 (0.5) | MDI (1.05) | Mw = 11800 Mn = 3830 D = 3.080 | −35 |
| PO-297 | 1,4-butanediol (0.5) | | PolyTHF1000 (0.5) | MDI (1.05) | Mw = 9320 Mn = 2370 D = 3.933 | −42 |
| PO-300 | DCA (0.75) | | PolyTHF1000 (0.25) | MDI (1.05) | Mw = 5960 Mn = 1780 D = 3.347 | −30 |
| PO-301 | DCA (0.25) | | PolyTHF1000 (0.75) | MDI (1.05) | | |
| PO-301-R | DCA (0.25) | | PolyTHF1000 (0.75) | MDI (1.05) | Mw = 27900 Mn = 5160 D = 5.411 | −52 |
| PO-302 | DSA (0.5) | | PolyTHF1000 (0.5) | MDI (1.05) | Mw = 12100 Mn = 2330 D = 5.205 | −52 |
| PO-303 | BA-DCA (0.25) | | PolyTHF1000 (0.75) | MDI (1.05) | Mw = 33000 Mn = 4310 D = 7.647 | −49 |
| PO-304 | BA-DCA (0.5) | | PolyTHF1000 (0.5) | MDI (1.05) | Mw = 40300 Mn = 17500 D = 2.306 | −43 |
| PO-305 | BA-DCA (0.75) | | PolyTHF1000 (0.25) | MDI (1.05) | Mw = 10500 Mn = 1910 D = 5.505 | −8, 107 |
| PO-306 | DCA (0.25) | Ethylene glycol (0.25) | PolyTHF1000 (0.5) | MDI (1.05) | Mw = 16700 Mn = 4240 D = 3.940 | −45 |
| PO-307 | DCA (0.5) | | PPG 1000 (0.5) | MDI (1.05) | Mw = 11500 Mn = 4810 D = 2.387 | −19 |
| PO-308 PO-321 | DCA (0.5) | | PolyTHF1000 (0.5) | HDI (1.05) | Mw = 13700 Mn = 5380 D = 2.538 | −1 |

-continued

| Reaction | Monomer | Additional Chain extender | Polyol | Diisocyanate | MW | Tg |
|---|---|---|---|---|---|---|
| PO-320 | BA-DCA (0.75) | | PPG 1000 (0.25) | MDI (1.05) | Mw = 12400 Mn = 4550 D = 2.713 | −12 |
| PO-322 | DCA (0.5) | | PolyTHF1000 (0.5) | MDI (0.525) HDI (0.525) | Mw = 23800 Mn = 6450 D = 3.691 | |
| PO-323 | DCA from lignin oil (0.5) | | PolyTHF1000 (0.5) | MDI (1.05) | Mw = 27600 Mn = 7330 D = 3.771 | −39 |
| PO-325 | BA-DCA (0.5) | | PolyTHF1000 (0.5) | MDI (1.05) | Mw = 21800 Mn = 7030 D = 3.095 | −35 |
| PO-327 | BA-DSA (0.5) | | PolyTHF1000 (0.5) | MDI (1.05) | Mw = 23300 Mn = 9790 D = 2.380 | −35 |
| PO-328 | BA-DCA (0.875) | | PolyTHF1000 (0.125) | MDI (1.05) | Mw = 15600 Mn = 7170 D = 2.171 | 25 |
| PO-329 | DCA (0.5) | | PolyTHF1000 (0.5) | MDI (0.7875) HDI (0.2625) | Mw = 23500 Mn = 8230 D = 2.856 | |
| PO-330-1 | DCA (0.5) | | PolyTHF650(0.5) | MDI (0.7875) HDI (0.2625) | Mw = 14700 Mn = 5260 D = 2.796 | |
| PO-330-2 | DCA (0.5) | | PolyPPG725 (0.5) | MDI (0.7875) HDI (0.2625) | Mw = 18900 Mn = 6160 D = 3.064 | 2 |
| PO-330-3 | DCA (0.5) | | PEG600 (0.5) | MDI (0.7875) HDI (0.2625) | | |
| PO-338-1 | DCA (0.5) | | PolyPPG725 (0.5) | MDI (0.79) HDI (0.26) | | −1 |
| PO-338-2 | DCA (0.25) | | PolyPPG725 (0.75) | MDI (0.92) HDI (0.13) | | −14 |
| PO-338-3 | DCA (0.75) | | PolyPPG725 (0.25) | MDI (0.66) HDI (0.39) | | 12 |
| PO-338-4 | DCA (0.875) | | PolyPPG725 (0.125) | MDI (0.59) HDI (0.46) | | |
| PO-339 | DCA (1) | | | MDI (1.05) | | |
| PO-340-1 | DCA (0.25) | 1,4-butanediol (0.25) | PolyTHF1000 (0.5) | MDI (1.05) | | −33 |
| PO-340-2 | BA-DCA (0.25) | 1,4-butanediol (0.25) | PolyTHF1000 (0.5) | MDI (1.05) | | −28 |
| PO-343 | DCA (0.75) | | PolyPPG 2000 (0.25) | MDI (1.05) | | −21 |
| PO-344 | BA-DCA (0.75) | | PolyPPG 2000 (0.25) | MDI (1.05) | | −21 |

The invention claimed is:

1. A thermoplastic polyurethane comprising lignin-derived monomers, lignin model compounds, or the products of their respective functionalization according to formula (Ib):

(Ib)

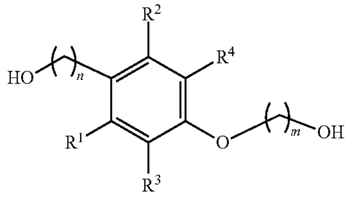

where:

$R^1$ and $R^2$ independently represent H or alkyl;

$R^3$ and $R^4$ independently represent H or oxy-alkyl;

n is 0, 1, 2, or 3; and m is an integer from 1 to 12.

2. The thermoplastic polyurethane according to claim 1, wherein:

$R^1$ and $R^2$ independently represent H or $C_{1-6}$ alkyl; and $R^3$ and $R^4$ independently represent H or oxy-$C_{1-6}$ alkyl.

3. The thermoplastic polyurethane according to claim 1, wherein:

$R^1$ and $R^2$ independently represent H or $CH_3$; and $R^3$ and $R^4$ independently represent H or $OCH_3$.

4. The thermoplastic polyurethane according to claim 1, comprising the reaction product of:

(a) an isocyanate composition;

(b) lignin-derived monomers, lignin model compounds or the products of their respective functionalization according to formula (Ib); and (c) a polyol composition.

5. The thermoplastic polyurethane according to claim 1, comprising the reaction product of:

(a) an isocyanate composition;

(b) lignin-derived monomers, lignin model compounds or the products of their respective functionalization according to formula (Ib);

(c) a polyol composition; and (d) an additional chain extender.

6. The thermoplastic polyurethane according to claim 5, wherein the isocyanate composition comprises an aromatic diisocyanate, an aliphatic diisocyanate, a cycloaliphatic diisocyanate, or a mixture of any of them.

7. The thermoplastic polyurethane according to claim 5, wherein the polyol composition comprises a polyether polyol, polyester polyol, polyacrylated polyol, polycarbonate polyol, polysiloxane polyol, or mixtures thereof, with a molecular weight from 200 g/mol to 8000 g/mol.

8. The thermoplastic polyurethane according to claim 5, wherein the polyol composition comprises lignin-derived monomers, lignin model compounds, or the products of their respective functionalization according to formula (Ib) as a repeating unit.

9. The thermoplastic polyurethane according to claim 5, wherein the additional chain extender composition comprises diols, diamines, and combinations thereof with 2 to 12 carbon atoms.

10. The thermoplastic polyurethane according to claim 5, wherein the equivalents of diisocyanate to active hydrogen containing components is from 0.3 to 2.

11. The thermoplastic polyurethane according to claim 5, wherein the molar ratio of the polyol component to the sum of lignin-derived monomers and additional chain extenders is from 99:1 to 1:99.

12. The thermoplastic polyurethane according to claim 1, wherein the lignin-derived monomers are present as an extract of depolymerized lignin comprising at least 80% by weight lignin-derived monomers of formula (Ib).

13. The thermoplastic polyurethane according to claim 1, wherein the lignin-derived monomers are present as an extract of depolymerized lignin comprising at least 90% by weight lignin-derived monomers of formula (Ib).

14. A product obtained by reaction extrusion, batch processing, solution polymerization, reaction injection molding, or cast polymerization of the thermoplastic polyurethane according to claim 1.

15. A method of synthesizing a thermoplastic polyurethane according to claim 1, the method comprising:

reacting a lignin derived monomer with an isocyanate composition and a polyol composition, wherein the lignin-derived monomer is chosen from lignin-derived monomers, lignin model compounds, or the products of their respective functionalization according to formula (Ib):

(Ib)

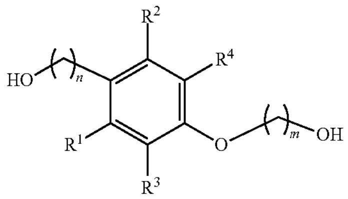

where:

$R^1$ and $R^2$ independently represent H or alkyl;

$R^3$ and $R^4$ independently represent H or oxy-alkyl;

n is 0, 1, 2, or 3; and m is an integer from 1 to 12.

* * * * *